United States Patent
Mendoza et al.

(10) Patent No.: US 9,295,659 B2
(45) Date of Patent: Mar. 29, 2016

(54) HIGH DOSE EXTENDED-RELEASE POTASSIUM CITRATE WAX MATRIX TABLET

(71) Applicants: Wendell G. Mendoza, Mandaluyong (PH); Rita Josefina M. Santos, Quezon (PH); Kennie U. Dee, Quezon (PH)

(72) Inventors: Wendell G. Mendoza, Mandaluyong (PH); Rita Josefina M. Santos, Quezon (PH); Kennie U. Dee, Quezon (PH)

(73) Assignee: UNITED LABORATORIES, INC., Mandaluyong (PH)

( * ) Notice: Subject to any disclaimer, the term of this patent is extended or adjusted under 35 U.S.C. 154(b) by 0 days.

(21) Appl. No.: 14/431,374

(22) PCT Filed: Feb. 28, 2013

(86) PCT No.: PCT/PH2013/000007
§ 371 (c)(1),
(2) Date: Mar. 26, 2015

(87) PCT Pub. No.: WO2014/133401
PCT Pub. Date: Sep. 4, 2014

(65) Prior Publication Data
US 2015/0272913 A1    Oct. 1, 2015

(51) Int. Cl.
*A61K 9/16* (2006.01)
*A61K 31/194* (2006.01)
*A61K 9/20* (2006.01)

(52) U.S. Cl.
CPC .............. *A61K 31/194* (2013.01); *A61K 9/2013* (2013.01); *A61K 9/2077* (2013.01); *A61K 9/2095* (2013.01)

(58) Field of Classification Search
USPC ................................ 514/15.4, 547, 557, 574
See application file for complete search history.

(56) References Cited

U.S. PATENT DOCUMENTS

| 4,904,478 A | 2/1990 | Walsdorf et al. |
| 2008/0131504 A1 | 6/2008 | Walsdorf, Sr. et al. |

FOREIGN PATENT DOCUMENTS

| CN | 102240272 A | 11/2011 |
| CN | 102488670 A | 6/2012 |
| WO | 2014051443 A1 | 4/2014 |

OTHER PUBLICATIONS

Website; http://www.aspenpharma.com.au/product_info/pi/Urocit-K_PI_25Mar10.pdf; Mar. 25, 2010.*
International Search Report—PCT/PH2012/000013—Dated Apr. 30, 2013.
International Search Report—Application No. PCT/PH2013/000007 dated Oct. 31, 2013.

* cited by examiner

*Primary Examiner* — Fereydoun G Sajjadi
*Assistant Examiner* — Pancham Bakshi
(74) *Attorney, Agent, or Firm* — Banner & Witcoff, Ltd.

(57) ABSTRACT

The present invention relates to a high dose extended-release potassium citrate tablet containing carnauba wax, which contains a first portion of melt- or heat-granulated carnauba wax and potassium citrate; and a second portion of non-granulated potassium citrate. The high dose extended-release potassium citrate tablet of this invention has robust batch-to-batch dissolution and friability; and leads to improved production capacity and reduced production cost.

10 Claims, No Drawings

HIGH DOSE EXTENDED-RELEASE POTASSIUM CITRATE WAX MATRIX TABLET

CROSS-REFERENCE TO RELATED APPLICATIONS

This application is a U.S. National Stage application under 35 U.S.C. §371 of International Application PCT/PH2013/000007 (published as WO 2014/133401 A1), filed Feb. 28, 2013. Benefit of the filing date of this application is hereby claimed. This application is hereby incorporated by reference in its entirety.

BACKGROUND OF THE INVENTION

Potassium citrate is used clinically to treat kidney stones by alkalizing the urinary pH and increasing urinary citrate concentration. However, its therapeutic efficacy is limited by its gastrointestinal complications such as irritation and ulcerations. Extended-release tablets of potassium citrate could minimize these side effects and have been shown to lead to sustained elevation of urinary pH and citrate concentration (Pak et al., 1984).

Considerable difficulties have been encountered in the preparation of extended-release matrix tablets containing potassium citrate. Potassium citrate is very soluble in water and the dosage required is very high. The only way to extend the release of potassium citrate tablet while keeping the tablet size acceptable for swallowing is to use a hydrophobic wax matrix, such as carnauba wax, wherein the total amount of inactive ingredients is below 25% w/w.

When the drug content is low, the carnauba wax can be dry mixed with the drug and other inactive ingredients prior to compression. For example, U.S. Pat. No. 4,904,478 teaches an extended-release wax matrix tablet of a highly water-soluble drug, sodium fluoride, wherein the carnauba wax, present at 35-70% w/w of the tablet weight, is dry mixed with the drug and other inactive ingredients prior to compression.

In the case of potassium citrate, because the drug dosage is high, the inactive ingredients including the extended-release agent(s) must be kept below 25% w/w to keep the tablet size acceptable for swallowing. If carnauba wax is used at less than 25% w/w, prior art teaches that the drug and carnauba wax should be heated until the carnauba wax liquefies, as described in Example 1 of US 2008/0131504 A1 (Mission Pharmacal, San Antonio, Tex., USA) to give an acceptable extended-release profile and friability. Friability is a measure of the durability of the tablet from the time it is compressed, to packaging, and to the time of use.

The process of US 2008/0131504A1 for making extended-release potassium citrate tablet containing carnauba wax is difficult. Heating until the carnauba wax liquefies requires a lot of time and then there is the problem of discharging the molten potassium citrate-carnauba wax mixture from the mixer. The cooled mass is extremely hard; therefore the molten mass must be poured into molds so that the cooled mixture is of appropriate size for feeding into a comminuting machine.

A simpler process for making the extended-release potassium citrate tablet is described in PCT/PH2012/000013, which surprisingly found that extended-release potassium citrate tablets containing carnauba wax could be produced without melting the wax. The potassium citrate-carnauba wax mixture is heated to a temperature below the temperature at which carnauba wax liquefies, and then discharged from the mixer as granules. The temperature is preferably higher than 55° C., and most preferably higher than 60° C. The cooled granulate can then be fed directly into a comminuting machine for size reduction, after which a lubricant is added, and the final mixture compressed into tablets. The tablet produced according to PCT/PH2012/000013 has the same dissolution profile as tablet produced by totally melting the wax. Hereafter, we will use melt-granulation and heat-granulation to refer to the processes described in US 2008/0131504A1 and PCT/PH2012/000013, respectively.

Mission Pharmacal, the innovator of the extended-release potassium citrate tablet, sells the tablet under the brand name Urocit-K, in three strengths: 5-meq, 10-meq, and 15-meq tablets. The daily dose of Urocit-K is 30-60 meq, which requires 6-12 tablets of the 5-meq, 3-6 tablets of the 10-meq, and 2-4 tablets of the 15-meq. Urocit-K is a wax matrix tablet containing potassium citrate, carnauba wax as extended-release agent, and magnesium stearate as lubricant.

Because of the large daily dose of potassium citrate, the preferred strength is the high dose 15-meq tablet. However, the 15-meq Urocit-K tablet, the only high dose tablet commercially available, has difficulty complying with the USP dissolution requirement. There is therefore a need for a robust high dose extended-release potassium citrate tablet that consistently passes USP dissolution requirement and with acceptable friability.

SUMMARY OF THE INVENTION

We have surprisingly found that high dose extended-release potassium citrate tablets can be produced by replacing a portion of the melt- or heat-granulated potassium citrate with non-granulated potassium citrate. Contrary to expectation, replacing a portion of the melt- or heat-granulated potassium citrate with non-granulated potassium citrate does not lead to tablets with poorer friability. The tablet of this instant invention has good friability and consistently passes the USP dissolution. Further, because melt- or heat-granulation is the most difficult step of the production process, replacing a portion of the melt- or heat-granulated potassium citrate with non-granulated potassium citrate increases production capacity and reduces production cost.

DETAILED DESCRIPTION OF THE INVENTION

Extended-release potassium citrate tablet must comply with USP 35. Dissolution is performed in 900 ml water, apparatus 2 at 50 rpm, and must comply with the following dissolution specifications:

TABLE 1

| (dissolution, 12 units) | | |
| --- | --- | --- |
| Time | All Units | Average |
| 30 min | 30-60% | 35-55% |
| 1 hour | 45-75% | 50-70% |
| 3 hour | ≥75% | ≥80% |

Friability was measured in an Erweka TAR20. Briefly, ten tablets were placed inside a baffled 287 mm ID drum. The drum was rotated at 25 rpm for 4 minutes. The difference in the total tablet weight before and after rotating the drum divided by the initial tablet weight is the friability. The desired friability for high dose extended-release potassium citrate tablet is not more than 3%.

Comparative Example 1

Three different commercial lots of 10-meq Urocit-K tablets were purchased, and subjected to USP 35 dissolution. The results are as follows:

TABLE 2

| Lot 1 (dissolution, 12 units) | | |
| --- | --- | --- |
| Time | Range | Average |
| 30 min | 43.6-47.6% | 45.2% |
| 1 hour | 57.9-61.1% | 60.4% |
| 3 hour | 87.9-97.4% | 91.7% |

TABLE 3

| Lot 2 (dissolution, 12 units) | | |
| --- | --- | --- |
| Time | Range | Average |
| 30 min | 41.2-44.5% | 43.3% |
| 1 hour | 54.7-58.9% | 57.7% |
| 3 hour | 82.5-89.4% | 87.7% |

TABLE 4

| Lot 3 (dissolution, 12 units) | | |
| --- | --- | --- |
| Time | Range | Average |
| 30 min | 42.8-44.7% | 43.6% |
| 1 hour | 56.4-59.0% | 57.4% |
| 3 hour | 85.5-88.4% | 86.5% |

All three lots comply with USP 35 requirement for extended-release potassium citrate tablet. The average dissolution at 30 min and 1 hour are close to the mean values of the USP specifications at 45% and 60%, respectively.

Example 2

Three batches of 10-meq tablets were prepared by using the heat-granulation technique of PCT/PH2012/000013. Each batch is 100,000 tablets. The formulation is given in Table 5.

TABLE 5

| Ingredient | mg/tablet | % w/w |
| --- | --- | --- |
| Potassium citrate•H2O | 1080 | 85 |
| Carnauba wax | 177 | 14 |
| Magnesium stearate | 13 | 1 |

The procedure is as follows:
1. The potassium citrate was comminuted in a Fitzmill D6, knives forward, using perforated screen mesh 8.
2. The comminuted potassium citrate from #1 was mixed with carnauba wax in a sigma mixer for 20 minutes.
3. The granule from #2 was comminuted in a Fitzmill D6, knives forward, using perforated screen mesh 12.
4. The granule from #3 was heated in a jacketed sigma mixer, with continued mixing. Heating was continued until the temperature reached 70° C., which is below the melting point of carnauba wax.
5. The granule from #4 was discharged into plastic drums and allowed to cool to room temperature.
6. The cooled granule from #5 was comminuted in a Fitzmill D6, knives forward, using perforated screen mesh 16.
7. Magnesium stearate was passed through mesh 30 and mixed with the comminuted granule of #6 in a sigma mixer for 2 minutes.
8. The granule from #7 was compressed into 18.9×8.6 mm elliptical tablet in a Stokes-Pennwalt rotary tablet press model 900.

Tablet hardness was 11-13 kp, and the friability for the three batches was less than 3%. The dissolution profile is as follows:

TABLE 6

| Batch 1 (dissolution, 12 units) | | |
| --- | --- | --- |
| Time | Range | Average |
| 30 min | 43.5-48.8% | 46.8% |
| 1 hour | 59.6-63.8% | 61.9% |
| 3 hour | 89.9-94.7% | 92.8% |

TABLE 7

| Batch 2 (dissolution, 12 units) | | |
| --- | --- | --- |
| Time | Range | Average |
| 30 min | 44.2-45.7% | 44.8% |
| 1 hour | 59.4-62.6% | 61.0% |
| 3 hour | 91.2-98.6% | 93.5% |

TABLE 8

| Batch 3 (dissolution, 12 units) | | |
| --- | --- | --- |
| Time | Range | Average |
| 30 min | 44.0-45.2% | 44.7% |
| 1 hour | 58.9-59.7% | 59.3% |
| 3 hour | 88.0-89.8% | 89.1% |

All three batches comply with USP 35 requirement for extended-release potassium citrate tablet. The average dissolution at 30 min and 1 hour are close to the mean values of the USP specifications at 45% and 60%, respectively.

Comparative Example 3

Three different commercial lots of 15-meq Urocit-K tablets were purchased. The tablet weight of the 15-meq is 1.5× of the 10-meq Urocit-K tablet indicating that the two strengths are multiples of each other. The USP dissolution results are as follows:

TABLE 9

| Lot 1 (dissolution, 12 units) | | |
| --- | --- | --- |
| Time | Range | Average |
| 30 min | 36.7-42.2% | 39.1% |
| 1 hour | 49.9-53.2% | 51.4% |
| 3 hour | 74.8-82.4% | 77.9% |

TABLE 10

| | Lot 2 (dissolution, 12 units) | |
|---|---|---|
| Time | Range | Average |
| 30 min | 37.1-40.2% | 38.7% |
| 1 hour | 50.9-61.0% | 55.2% |
| 3 hour | 79.7-82.8% | 80.8% |

TABLE 11

| | Lot 3 (dissolution, 12 units) | |
|---|---|---|
| Time | Range | Average |
| 30 min | 35.2-39.0% | 37.2% |
| 1 hour | 49.9-52.2% | 51.1% |
| 3 hour | 74.2-82.8% | 79.2% |

Two of the three lots fail USP dissolution. Further, the average values for the 30 min and 1 hour are close to the lower limits of the USP dissolution of 35% and 50%, respectively, indicating the formulation is not robust.

Example 4

Three batches of 15-meq tablets were prepared by using the heat-granulation technique of PCT/PH2012/000013. Each batch is 67,000 tablets. The formulation in w/w percent is the same as Example 2, except that the tablet weight is 1.5× (1905 mg). The process of preparation is the same as Example 2 except that the granule was compressed into 22.5×9.3 mm elliptical tablets with hardness of 11-14 kp. Friability was less than 3% for the three batches. Dissolution was performed according to USP 35. The results are as follows:

TABLE 12

| | Lot 1 (dissolution, 12 units) | |
|---|---|---|
| Time | Range | Average |
| 30 min | 37.9-41.5% | 39.5% |
| 1 hour | 51.6-56.2% | 54.5% |
| 3 hour | 82.1-87.3% | 84.5% |

TABLE 13

| | Lot 2 (dissolution, 12 units) | |
|---|---|---|
| Time | Range | Average |
| 30 min | 36.1-38.2% | 37.1% |
| 1 hour | 48.9-53.2% | 50.2% |
| 3 hour | 73.2-80.9% | 76.8% |

TABLE 14

| | Lot 3 (dissolution, 12 units) | |
|---|---|---|
| Time | Range | Average |
| 30 min | 35.6-39.6% | 37.0% |
| 1 hour | 49.9-52.1% | 51.2% |
| 3 hour | 74.0-82.9% | 78.2% |

Two of the three batches fail USP dissolution. Further, the average values for the 30 min and 1 hour are close to the lower limits of the USP dissolution of 35% and 50%, respectively, indicating that this high dose extended-release tablet prepared according to prior art is not robust.

Example 5

Three formulations of 15-meq tablets with varying concentrations of carnauba wax were prepared by using the heat-granulation technique of PCT/PH2012/000013. The formulations are given in Table 15:

TABLE 15

| | 15-meq Tablets (mg/tablet) | | |
|---|---|---|---|
| Ingredient | Example 5A | Example 5B | Example 5C |
| Potassium citrate•H2O | 1620 | 1620 | 1620 |
| Carnauba wax | 223 (12%) | 182 (10%) | 133 (7.5%) |
| Magnesium stearate | 19 | 18 | 18 |

The Process of preparation is the same as Example 2. The granules were compressed into 22.5×9.3 mm elliptical tablets. The results are as follows:

TABLE 16

| | Example 5A (dissolution, 12 units) | |
|---|---|---|
| Time | Range | Average |
| 30 min | 39.3-43.8% | 40.2% |
| 1 hour | 53.2-57.7% | 54.6% |
| 3 hour | 85.1-87.4% | 86.7% |

The tablet hardness was about 10 kp, and friability was less than 3%. Note that reducing the carnauba wax from 14% in Example 4 to 12% in Example 5A did not change the mean dissolution values for the 30 min and 1 hour time points significantly.

TABLE 17

| | Example 5B (dissolution, 12 units) | |
|---|---|---|
| Time | Range | Average |
| 30 min | 47.0-50.1% | 48.5% |
| 1 hour | 62.2-65.6% | 63.7% |
| 3 hour | 95.4-100.0% | 96.9% |

The maximum tablet hardness was 8.9 kp. While this formulation with 10% heat-granulated carnauba wax passes USP dissolution, the friability of 5.8% was not acceptable.

TABLE 18

| | Example 5C (dissolution, 12 units) | |
|---|---|---|
| Time | Range | Average |
| 30 min | 53.2-56.7% | 54.8% |
| 1 hour | 70.3-74.1% | 71.9% |
| 3 hour | 95.9-100.0% | 98.1% |

The maximum tablet hardness was 7.0 kp, and these tablets with 7.5% heat-granulated carnauba wax failed friability (capped tablets) and USP dissolution.

The examples of the prior art—Comparative Example 3, Example 4, Example 5A, Example 5B, and Example 5C—show that it is difficult to achieve a good balance of friability and robust dissolution for high dose extended-release potassium citrate tablet when all of the potassium citrate is melt- or heat-granulated with the carnauba wax.

Example 6

Three formulations of 15-meq tablets with varying ratios of non-granulated and heat-granulated potassium citrate were prepared. The heat-granulated potassium citrate was prepared according to steps 1-6 of Example 2. This potassium citrate-carnauba wax heat-granulate is 85.9% potassium citrate and 14.1% carnauba wax.

To prepare the non-granulated potassium citrate for dry addition, potassium citrate was comminuted in a Fitzmill D6, knives forward, medium speed using perforated screen mesh 14.

The heat-granulated potassium citrate, and non-granulated potassium citrate were combined according to Table 19:

TABLE 19

15-meq Tablets (mg/tablet)

| | Example 6A 85/15 | Example 6B 80/20 | Example 6C 75/25 |
|---|---|---|---|
| Heat-granulated potassium citrate-carnauba wax | 1603 mg | 1509 mg | 1414 mg |
| Non-granulated potassium citrate monohydrate | 243 mg | 324 mg | 405 mg |
| Magnesium stearate | 19 mg | 19 mg | 18 mg |

The heat-granulated potassium citrate and the non-granulated potassium citrate were mixed in a Sigma mixer for 20 minutes. Magnesium stearate (passed thru mesh 30) was then added, and mixed for 3 minutes. The final granule was compressed into 22.5×9.3 mm elliptical tablet in a Stokes-Pennwalt rotary tablet press model 900.

Example 6A contains 15% non-granulated potassium citrate, Example 6B contains 20% non-granulated potassium citrate, and Example 6C contains 25% non-granulated potassium citrate. The formulations of Table 19 in percent w/w is given in Table 20:

TABLE 20

15-meq Tablets in mg/tablet (% w/w)

| Ingredient | Example 6A | Example 6B | Example 6C |
|---|---|---|---|
| Potassium citrate•H2O | 1620 (86.9%) | 1620 (87.5%) | 1620 (88.2%) |
| Carnauba wax | 226 (12.1%) | 213 (11.5%) | 199 (10.8%) |
| Magnesium stearate | 19 (1%) | 19 (1%) | 18 (1%) |

These tablets were subjected to USP dissolution. Results are as follows:

TABLE 21

Example 6A (dissolution, 12 units)

| Time | Range | Average |
|---|---|---|
| 30 min | 42.4-45.6% | 43.6% |
| 1 hour | 57.5-59.5% | 58.2% |
| 3 hour | 88.9-92.9% | 90.4% |

The tablet of Example 6A passes the USP dissolution, with the 30 min and 1 hour data close to the mean values of the USP dissolution specifications of 45% and 60%, respectively. The tablet hardness was 10 kp and friability was 1.9%. This example shows that combining heat-granulated potassium citrate and non-granulated potassium citrate according to this instant invention leads to high dose extended-release potassium citrate with good friability and robust dissolution.

TABLE 22

Example 6B (dissolution, 12 units)

| Time | Range | Average |
|---|---|---|
| 30 min | 41.8-47.1% | 44.3% |
| 1 hour | 55.8-59.5% | 58.1% |
| 3 hour | 88.7-93.0% | 90.9% |

The tablet of Example 6B passes the USP dissolution, with the 30 min and 1 hour data close to the mean values of the USP dissolution specifications of 45% and 60%, respectively. The tablet hardness was 11 kp and friability was 1.4%. This example shows that combining heat-granulated potassium citrate and non-granulated potassium citrate according to this instant invention leads to high dose extended-release potassium citrate with good friability and robust dissolution.

TABLE 23

Example 6C (dissolution, 12 units)

| Time | Range | Average |
|---|---|---|
| 30 min | 44.2-50.3% | 46.2% |
| 1 hour | 58.5-65.6% | 62.2% |
| 3 hour | 97.5-100.0% | 98.2% |

The tablet of Example 6C passes the USP dissolution, with the 30 min and 1 hour data close to the mean values of the USP dissolution specifications of 45% and 60%, respectively. The tablet hardness was 11.5 kp and friability was 1.8%. This example shows that combining heat-granulated potassium citrate and non-granulated potassium citrate according to this instant invention leads to high dose extended-release potassium citrate with good friability and robust dissolution.

Example 7

Three additional large production-scale batches of 15-meq tablets according to Example 6B were prepared. Each batch is 83,000 tablets. Tablet hardness of the three batches was 10-12 kp, and friability was 1-2%. Dissolution was performed according to USP 35. The results are as follows:

TABLE 24

Example 7 - Batch 1 (dissolution, 12 units)

| Time | Range | Average |
|---|---|---|
| 30 min | 45.4-47.1% | 46.2% |
| 1 hour | 59.6-62.9% | 61.2% |
| 3 hour | 89.3-95.4% | 92.9% |

TABLE 25

Example 7 - Batch 2 (dissolution, 12 units)

| Time | Range | Average |
|---|---|---|
| 30 min | 44.7-45.9% | 45.3% |
| 1 hour | 60.5-62.9% | 61.4% |
| 3 hour | 93.3-97.0% | 95.3% |

TABLE 26

Example 7 - Batch 3 (dissolution, 12 units)

| Time | Range | Average |
|---|---|---|
| 30 min | 44.8-48.1% | 46.3% |
| 1 hour | 59.2-61.5% | 60.3% |
| 3 hour | 89.9-93.3% | 92.1% |

The above data clearly shows robust batch-to-batch dissolution and friability of the high dose extended-release potassium citrate tablets prepared according to this instant invention.

Example 8

A melt-granulate of potassium citrate-carnauba wax was prepared according to the formulation of Table 27:

TABLE 27

| Ingredient | % w/w |
|---|---|
| Potassium citrate•H2O | 85.9 |
| Carnauba wax | 14.1 |

The procedure is as follows:
1. The potassium citrate was comminuted in a Fitzmill D6, knives forward, using perforated screen mesh 8.
2. The comminuted potassium citrate from #1 was mixed with carnauba wax in a sigma mixer for 20 minutes.
3. The granule from #2 was comminuted in a Fitzmill D6, knives forward, using perforated screen mesh 12.
4. The granule from #3 was heated in a jacketed sigma mixer, with continued mixing. Heating was continued until the carnauba wax was fully melted (above 80° C.), and for an additional 10 minutes thereafter.
5. The liquid mass from #4 was poured into 2"×2"×2" molds, and allowed to cool to room temperature.
6. The blocks from #5 were comminuted in a Fitzmill D6, knives forward, using perforated screen mesh 16.

Example 9

Two large production-scale batches of 15-meq tablets according to Example 6B were prepared, but replacing the heat-granulated potassium citrate-carnauba wax with the melt-granulate of Example 8. Each batch is 83,000 tablets. Tablet hardness of the two batches was 10-12 kp, and friability was less than 3%. Dissolution was performed according to USP 35. The results are as follows:

TABLE 24

Example 9 - Batch 1 (dissolution, 12 units)

| Time | Range | Average |
|---|---|---|
| 30 min | 45.3-47.4% | 45.7% |
| 1 hour | 58.9-62.8% | 61.6% |
| 3 hour | 90.4-95.7% | 92.7% |

TABLE 25

Example 9 - Batch 2 (dissolution, 12 units)

| Time | Range | Average |
|---|---|---|
| 30 min | 45.4-48.0% | 46.5% |
| 1 hour | 61.1-65.1% | 62.7% |
| 3 hour | 89.4-94.6% | 92.3% |

The above data clearly shows robust batch-to-batch dissolution and friability of the high dose extended-release potassium citrate tablets prepared according to this instant invention. Further, melt-granulated potassium citrate-carnauba wax can be used in place of the heat-granulated potassium citrate-carnauba wax, with the same results.

This instant invention encompasses all the combinations of melt-/heat-granulated potassium citrate and non-granulated potassium citrate, where the melt-/heat-granulated potassium citrate can contain carnauba wax levels different from the above embodiments. It is within the capability of a person ordinarily skilled in the art to conduct simple experiments to determine the optimum ratio of melt-/heat-granulated and non-granulated potassium citrate to arrive at a formulation with robust batch-to-batch dissolution and friability.

The invention claimed is:

1. A high dose extended-release potassium citrate tablet containing carnauba wax, which comprises: a first portion of melt- or heat-granulated potassium citrate and carnauba wax; and a second portion of non-granulated potassium citrate.

2. The formulation according to claim 1, wherein the high dose potassium citrate tablet contains more than 10-meq of potassium citrate.

3. The formulation according to claim 2, wherein the high dose potassium citrate tablet contains 15-meq of potassium citrate.

4. The formulation according to claim 1, wherein the non-granulated potassium citrate is 10-30% of the total amount of potassium citrate.

5. The formulation according to claim 4, wherein the non-granulated potassium citrate is 15-25% of the total amount of potassium citrate.

6. The formulation according to claim 1 wherein the carnauba wax in the melt- or heat-granulate is 7-25% of the total weight of the granulate.

7. The formulation according to claim 6, wherein the carnauba wax in the melt- or heat-granulate is 10-18% of the total weight of the granulate.

8. The high dose extended-release potassium citrate tablet of claim 1, comprising 15-meq potassium citrate, wherein the first portion of melt- or heat-granulated potassium citrate contains 10-18% w/w of carnauba wax and wherein the second portion of non-granulated potassium citrate comprises 15-25% of the total amount of potassium citrate.

9. The formulation according to claim 8, which further comprises a lubricant.

10. The formulation according to claim 9, wherein the lubricant is magnesium stearate.

* * * * *